United States Patent [19]

Horres, Jr.

[11] Patent Number: 4,634,679
[45] Date of Patent: Jan. 6, 1987

[54] METHOD OF DETERMINING ADHESION OF A LIQUID SAMPLE

[75] Inventor: C. Russell Horres, Jr., Chapel Hill, N.C.

[73] Assignee: Becton Dickinson and Company, Franklin Lakes, N.J.

[21] Appl. No.: 440,541

[22] Filed: Nov. 10, 1982

[51] Int. Cl.$^4$ .......................... G01N 1/10; G01N 33/48
[52] U.S. Cl. ...................................... 436/63; 436/174; 436/178
[58] Field of Search ................. 436/63, 174, 175, 177, 436/178; 73/58, 64.4, 864.01, 864.02, 864.11, 864.12, 864.14, 864.22; 366/106, 341, 262, 139

[56] References Cited

U.S. PATENT DOCUMENTS

| | | | |
|---|---|---|---|
| 3,463,614 | 8/1969 | Leslie | 436/69 |
| 3,464,800 | 9/1969 | Gerarde | 422/100 |
| 3,898,982 | 8/1975 | Katsuda | 73/864.02 X |
| 4,003,262 | 1/1977 | Gerarde | 73/864.12 |
| 4,117,728 | 10/1978 | Johnson | 73/864.18 |

OTHER PUBLICATIONS

Adams et al, American Journal of Physiology, vol. 240, pp. H99–H108, 1981.
Adams et al, Trans. Am. Soc. Artif. Intern. Organs, vol. 27, pp. 219–224, 1981.
Muggli et al, J. Lab. Clin. Med., vol. 95, No. 2, pp. 195–207, (1980).
Cazenave et al., J. Lab. Clin. Med., vol. 86, No. 4, pp. 551–563 (1975).
Kinlough–Rathbone et al, J. Lab. Clin. Med., vol. 90, No. 4, pp. 707–719 (1977).
Adams et al, Chemical Abstracts, vol. 98, No. 98:51119b (1983).
Cazenave et al, J. Lab. Clin. Med., vol. 93, No. 1, pp. 60–70 (Jan. 1979).
Cazenave et al, Chemical Abstracts, vol. 80, #57167r, 1974.

Primary Examiner—Barry S. Richman
Assistant Examiner—Robert J. Hill, Jr.
Attorney, Agent, or Firm—Elliot M. Olstein

[57] ABSTRACT

Adhesion of a liquid sample is accomplished by drawing same into a capillary tube, followed by forming an immiscible fluid column at each end of the liquid sample in the tube, pulsing the liquid sample between the fluid columns and determining the portion of the liquid sample which adheres to the tube surface. The procedure may be employed for measuring platelet adhesion for a blood sample.

6 Claims, 5 Drawing Figures

METHOD OF DETERMINING ADHESION OF A LIQUID SAMPLE

This invention relates to mixing, and more particularly, to a new and improved process for mixing which may be used for measuring platelet adhesion.

In many cases, it is highly desirable to mix a microsample of a liquid. Although effective mixing processes exist for larger samples, such as mechanical stirring or inversion of tubes, such techniques are not usually applicable to the mixing of microliter samples.

In accordance with the present invention, there is provided a procedure for the mixing of microliter samples.

More particularly, a sample of a material, such as a liquid, is drawn into a tube to form a liquid column of the sample in the tube. Thereafter, a column of fluid which is immiscible and non-reactive with the sample is provided in the tube, at each end of the liquid column, followed by pulsing the material sample between the fluid columns to effect mixing thereof.

The sample which is mixed is generally a liquid sample, and the fluid which is used for forming a column at both ends of the liquid is a fluid which will not react with the liquid. In most cases, the fluid employed for providing such column is a gas (preferably air).

In accordance with a preferred embodiment, the sample is a microsample and the tube is a capillary tube.

The term "microsample" or "microliter sample" as employed herein means a sample volume which does not exceed 100 microliters.

The term "mixing" as used herein includes physical mixing of a material or materials, and mixing of two materials for the purposes of reaction therebetween.

The liquid sample in the capillary tube, which is positioned between two columns of immiscible fluid may be conveniently mixed by causing the liquid to reciprocate at a controlled rate by application of a reciprocating force to the fluid columns, such as by an air pump. The rate is controlled in a manner such that the movement of liquid being mixed does not exceed the length of either column of fluid so that the liquid remains within the capillary tube.

Controlled reciprocation can be obtained by one of several means. For example, a pump consisting of a motor driven wheel to which a connecting rod assembly is fitted in such a manner as to cause a piston within a cylinder to move a controlled distance in a reciprocating fashion depending on the diameter of said wheel, may be used to create a reciprocating fluid column. The reciprocating fluid column may be connected to the capillary tube containing the liquid sample by a means such as a flexible tube. When using gas as the mixing fluid, it is often desirable to seal one end of the capillary tube to help confine the motion of the sample.

During the mixing of the liquid in the capillary tube, the temperature of such sample can be controlled, if desired, by application of heat or by cooling. Thus, the mixing can be accomplished at controlled conditions.

The mixing technique hereinabove described has particularly applicability for the mixing of a blood sample, with one or more additives.

In accordance with another aspect of the invention, there is provided a method for determining platelet adhesion, which incorporates the mixing technique of the present invention.

As known in the art, platelet function can be tested by determining the ability of platelets to adhere to solid surfaces, such as glass. In accordance with a prior art procedure, a 5 to 10 ml sample of blood is caused to flow through a column of packed glass beads, followed by counting of the platelets in the sample which pass through the column and comparison of such platelet count with a corresponding blood sample which has not been passed through the column to provide a measure of the percentage of platelets removed (platelet adhesion).

In accordance with the present invention, platelet adhesion may be determined by mixing a defined microsample of blood in a glass capillary tube between two fluid columns by the procedure hereinabove described, followed by counting the number of platelets remaining in the mixed sample and comparing such platelet count with an unmixed defined blood sample to provide a measure of the percentage of platelets removed (platelet adhesion).

The procedure of the present invention is an improvement over the hereinabove described glass bead technique in that smaller samples are required, the possibility of trapping of platelet to platelet aggregates in the bead material is eliminated, whereby the test is more representative of adhesion characteristics, and the problems associated with poorly defined flow characteristics through the beads are also eliminated.

BRIEF DESCRIPTION OF THE DRAWINGS

The invention will be further described with respect to the following drawings wherein:

Referring now to FIGS. 1 and 2 of the drawings, there is shown a glass precision bore capillary tube 10, including a calibrated mark or indicia 11 of the sample volume to be drawn into the capillary tube. The blood sample 12 is taken from a finger or from a tube of citrated blood and drawn up to the indicia mark 11.

Figure 1:
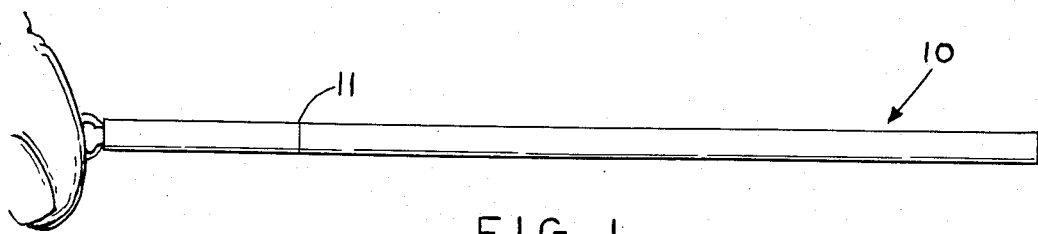
FIGS. 1–5 of the drawings depict a technique for measuring platelet adhesion in accordance with the invention.
Figure 2:
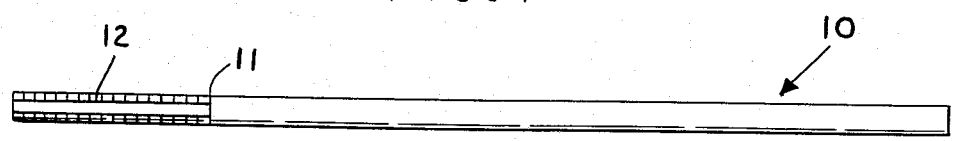
Figure 3:
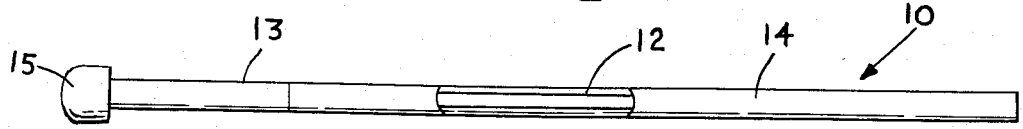

Subsequently (FIG. 3) two air columns are formed on either side of the sample 12, with the first column being schematically designated as 13 and the second column being schematically designated as 14, and one end of the tube is closed by a cap 15. The blood sample 12 between columns 13 and 14 is shown in FIG. 3 of the drawings.

Figure 4:
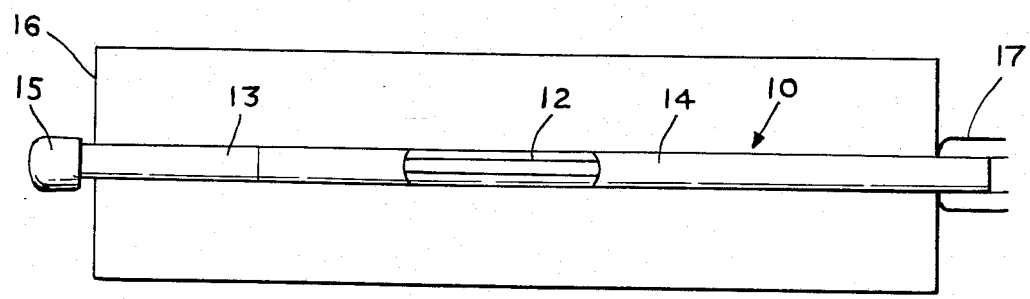

In FIG. 4 of the drawings, the capillary tube 10 is placed in a 37° C. incubating block 16 such that heat may be transferred to the blood sample and the capillary tube is connected to a positive displacement reciprocating pump (not shown) through a suitable connecting means, schematically shown as 17.

Figure 5:
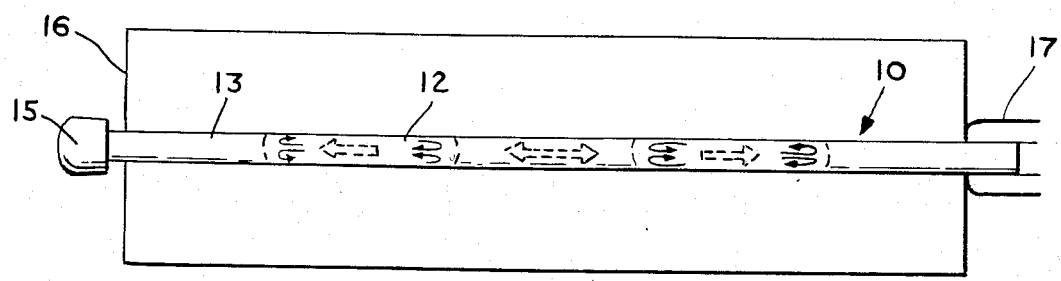

As generally shown in FIG. 5, the sample 12 is caused to reciprocate within the capillary tube 10 between the air columns 13 and 14, with such pulsing or reciprocal action causing mixing of the sample 12.

The sample 12 in tube 10 moves a distance in each direction which does not exceed the length of the original air columns 13 and 14 so as to retain the sample within tube 10.

After mixing, the sample is expelled into a platelet counting diluent for analysis on a whole blood platelet counter, of a type known in the art, in order to determine the amount of platelets which have adhered to the surface of the glass capillary tube, as hereinabove described.

Although the embodiment has been described with reference to use of a glass tube, it is to be understood that other materials could be used provided that they provide a suitable substrate for measuring platelet adhesion.

Similarly, the embodiment may be modified by use of a capillary tube having a coating on the interior surface thereof which is formed from a material or materials which can be used to differentially diagnose platelet function defects. For example, a capillary tube may have its interior surface coated with collagen, which will induce platelets to adhere more strongly than glass.

It is also to be understood that although the embodiment has been described with reference to a blood sample, and in particular to a platelet retention test, the mixing method of the invention is not limited to such a sample and/or test.

It is further to be understood that although the embodiment has been described with reference to the use of air columns, other gas columns could be used and/or the columns may be formed from a liquid which is immiscible with the sample to be mixed.

The invention will be further described with reference to the following example which illustrates a platelet adhesion test which incorporates the present invention; however, the scope of the invention is not to be limited thereby:

EXAMPLE

1. Whole blood is collected in sodium citrate at 0.0038 mg/ml.
2. A 10 μl sample is drawn into the center of a 0.04 mm inside diameter×1.45 mm outside diameter×127 mm long precision bore glass capillary tube.
3. One end of the tube is capped with a rubber seal and the other connected to a positive displacement reciprocating pump adjusted to allow a 34 mm displacement of the sample each cycle.
4. The tube, so connected, is placed into a thermostatically controlled 37° C. heating block and cycled at 90 strokes per minute for a period of 5 minutes.
5. At the end of the reaction the blood is expelled into a Unopette counting reservoir and counted on a UF-100 whole blood platelet counter.
6. Percentage platelet retention is determined by comparing the platelet count of the mixing sample with the platelet count of the unmixed blood.

Numerous modifications and variations of the present invention are possible in light of the above teachings and, therefore, within the scope of the appended claims, the invention may be practiced otherwise than as particularly described.

What is claimed is:

1. A method for determining platelet adhesion for a blood sample, comprising:
   placing a microsample of blood in a capillary tube having an interior surface to form a column of blood sample therein;
   forming a fluid column in the tube at each end of the blood sample column, said fluid being immiscible with the blood sample;
   pulsing the blood sample column in the tube between the fluid columns to thereby cause adhesion of platelets in the blood to the interior surface of the tube; and
   withdrawing the blood sample from the tube; and
   determining platelets in the blood sample which adhere to the interior surface of the tube.

2. The method of claim 1 wherein the interior surface of the tube includes a collagen coating.

3. The method of claim 1 wherein the tube is a glass tube.

4. The method of claim 1, wherein platelets in the blood sample which adhere to the interior surface of the tube are determined by comparing a platelet count of the blood sample pulsed in the tube with a platelet count of blood which is not subjected to said pulsing treatment.

5. The method of claim 1 wherein the fluid columns are gas columns.

6. The method of claim 5 wherein the gas columns are air.

* * * * *